United States Patent [19]

Sisti et al.

[11] Patent Number: 4,644,779

[45] Date of Patent: Feb. 24, 1987

[54] METHOD AND EQUIPMENT TO PERFORM POROSIMETRIC ANALYSES

[75] Inventors: Giorgio Sisti, Milan; Pietro Italiano, Cernusco Sul Naviglio; Ermete Riva, Merate; Bruno Tosi, Carate Brianza, all of Italy

[73] Assignee: Carlo Erba Strumentazione S.p.A., Italy

[21] Appl. No.: 742,636

[22] Filed: Jun. 10, 1985

Related U.S. Application Data

[63] Continuation of Ser. No. 393,603, Jun. 30, 1982, abandoned.

[30] Foreign Application Priority Data

Jul. 9, 1981 [IT] Italy .............................. 22820 A/81

[51] Int. Cl.$^4$ ............................................ G01N 15/08
[52] U.S. Cl. ........................................ 73/38; 73/432.1
[58] Field of Search ............... 73/38, 432 R, 314, 307, 73/432; 137/557

[56] References Cited

U.S. PATENT DOCUMENTS

| | | | |
|---|---|---|---|
| 2,392,637 | 1/1946 | Boehler | 73/38 |
| 3,039,293 | 6/1962 | Reddick et al. | 73/38 |
| 3,643,493 | 2/1972 | Vitousky | 73/38 |
| 3,859,843 | 1/1975 | Lowell | 73/38 |
| 3,882,714 | 5/1975 | Libal et al. | 73/38 |
| 3,947,665 | 3/1976 | Hundley | 364/509 |
| 4,028,939 | 6/1977 | Fletcher et al. | 364/510 X |
| 4,170,129 | 10/1979 | Lowell | 73/38 |
| 4,203,317 | 5/1980 | Gupta | 73/38 |
| 4,272,983 | 6/1981 | Sista et al. | 73/38 |
| 4,562,726 | 1/1986 | Barnaby | 73/38 |

FOREIGN PATENT DOCUMENTS

| | | | |
|---|---|---|---|
| 0409426 | 2/1945 | Italy | 73/38 |
| 2039058 | 7/1980 | United Kingdom | 73/38 |

OTHER PUBLICATIONS

IEEE Standard Dictionary of Electrical and Electronic Terms, 2nd Ed., May 12, 1978, F. Jay-Editor; pp. 171, 178, (1977), Au246.

Primary Examiner—Daniel M. Yasich
Attorney, Agent, or Firm—Lerner, David, Littenberg, Krumholz & Mentlik

[57] ABSTRACT

A method for performing porosimetric analyses and apparatus therefor are disclosed. In particular, a method for performing porosimetric anaylses by the so-called mercury method is disclosed, wherein volumetric variations of mercury placed in a vessel are recorded. These variations are due to mercury penetration into the pores of a solid sample placed in the vessel under the mercury pressure variations. In the method disclosed, additional porosimetric information is obtained by reducing the pressure from a maximum value as a predetermined function of time. For example, the pressure reduction can be at a constant rate. Simultaneously, volume variations of the mercury exiting the sample pores are detected as the pressure decreases. This additional detection, when performed in relation to and/or in addition to the traditional measurement during pressure increase, provides a pressure/volume mercury curve which gives further data on the porosimetric characteristics of the sample, in particular related to the shape of the pores in the sample.

13 Claims, 5 Drawing Figures

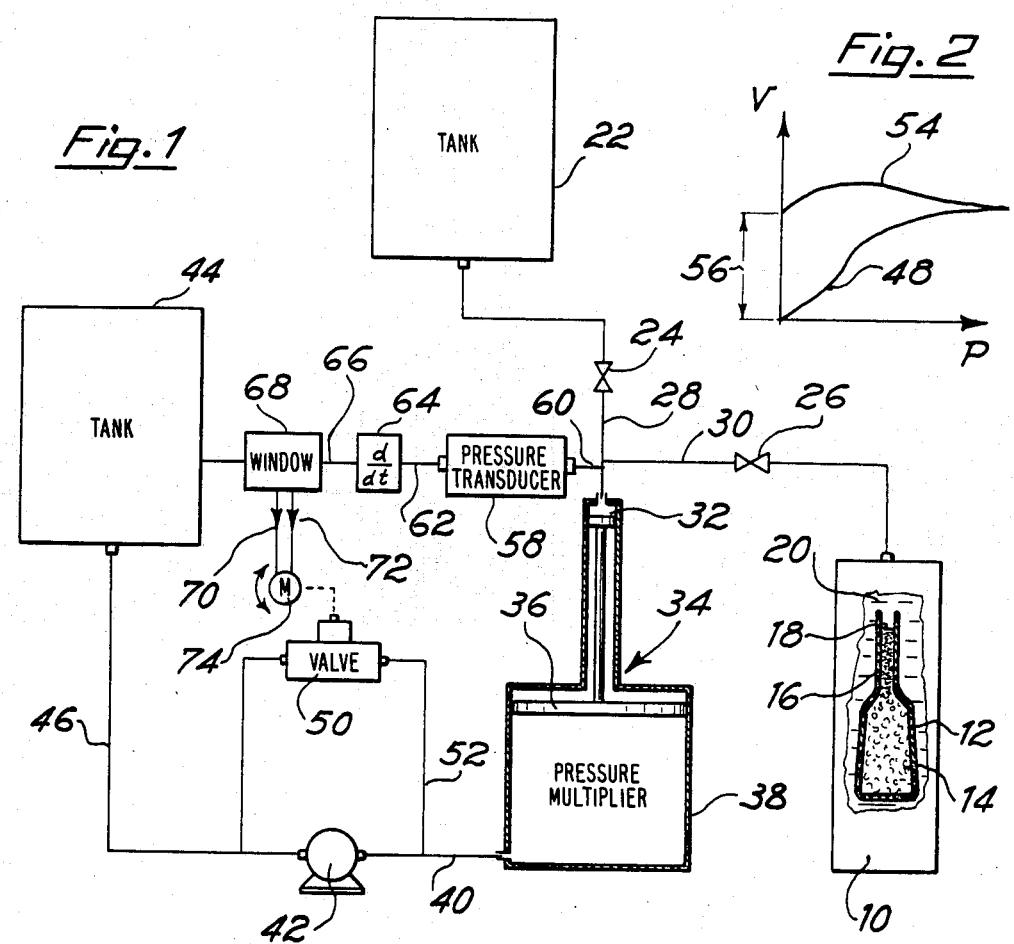
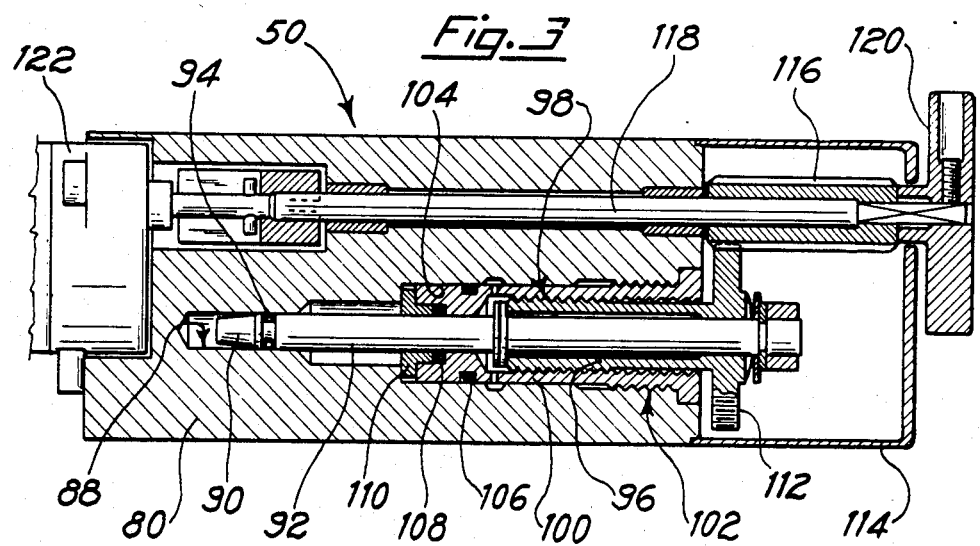

METHOD AND EQUIPMENT TO PERFORM POROSIMETRIC ANALYSES

This is a continuation of application Ser. No. 393,603, filed June 30, 1982 and now abandoned.

BACKGROUND OF THE INVENTION

1. Field of the Invention

The present invention concerns methods and apparatus for performing porosimetric analysis on solid samples.

2. Description of the Prior Art

According to known techniques, porosimetric analyses are performed by a process in which a solid sample is introduced into a test vessel together with a quantity of a suitable liquid, such as mercury. The liquid is then subjected to an increasing pressure. The volumetric variations of the liquid which is due to the penetration of the same into the pores of the sample is then detected as pressure varies.

By this known process, it is possible to trace a pressure-volume mercury curve, on the basis of which, and according to a known formula, it is possible to obtain a size distribution of the sample's pores, and information on the same sample.

During this test very high pressure values (around 2000 atmospheres) are reached and it is clear that at the end of same it is necessary to lower pressure to values substantially equal to the ambient ones.

During this pressure reduction, the test liquid, in particular mercury, obviously tends to come out of some of the pores which it had penetrated during pressure increase. In particular it tends to come out of the pores which present an open configuration, while, on the contrary, it tends to remain inside pores which present an almost closed configuration. Therefore, a lowering pressure-volume mercury curve is obtained which presents, together with the pressure-volume mercury curve traced during the pressure increase phase, a hysteretic course, allowing indications on the shape of the sample pores to be obtained. However, these indications are relatively fragmentary and partial, in that they are obtained up to now in correspondence to one or more pressure values, practically only in correspondence to the point corresponding to the return to ambient values as well as to the point of maximum pressure value.

SUMMARY OF THE INVENTION

It has now been proved, after tests carried out by the Applicant, that much wider and much more reliable information can be obtained if the decreasing pressure curve is obtained following a law predetermined in time, in particular at constant speed, or in any way such as to allow control on the rate of pressure decrease.

Therefore, the present invention relates to a method for porosimetric analyses of the above described type, wherein the stage of pressure reduction is performed according to a law predetermined in time and wherein the volume variations of the concerned liquid, in particular mercury, are detected, when pressure decreases according to said law. This law advantageously considers a pressure reduction at constant speed, as obtained by detecting the pressure of the liquid concerned, by taking a derivative of same with respect to time and by controlling a pressure exhaust device as a function of the instant value of the derivative.

The invention also concerns apparatus to perform said method and comprising, in a known circuit for pressure increase in a porosimeter having a low pressure circuit with a fluid feeding a pressure multiplier and then a high pressure circuit: detection means for high pressure; a device to correlate said detected high pressure with time; and control means for an exhaust valve operating on said low pressure circuit, under the control of said device. Said valve is preferably a needle valve with cone-shaped shutter and cylindrical seat.

BRIEF DESCRIPTION OF THE DRAWINGS

FIG. 1 is a diagrammatical view showing a pressurization circuit of a porosimeter, including an apparatus for the control of pressure exhaust, according to the present invention.

FIG. 2 is an example of a pressure-volume diagram which can be obtained in a complete porosimetric analysis when carried out by means of the apparatus of FIG. 1.

FIGS. 3 and 4 are axial cross-sections, angularly offset to each other and showing a pressure reduction valve for the apparatus of FIG. 1.

DESCRIPTION OF THE PREFERRED EMBODIMENT

Figure 4:
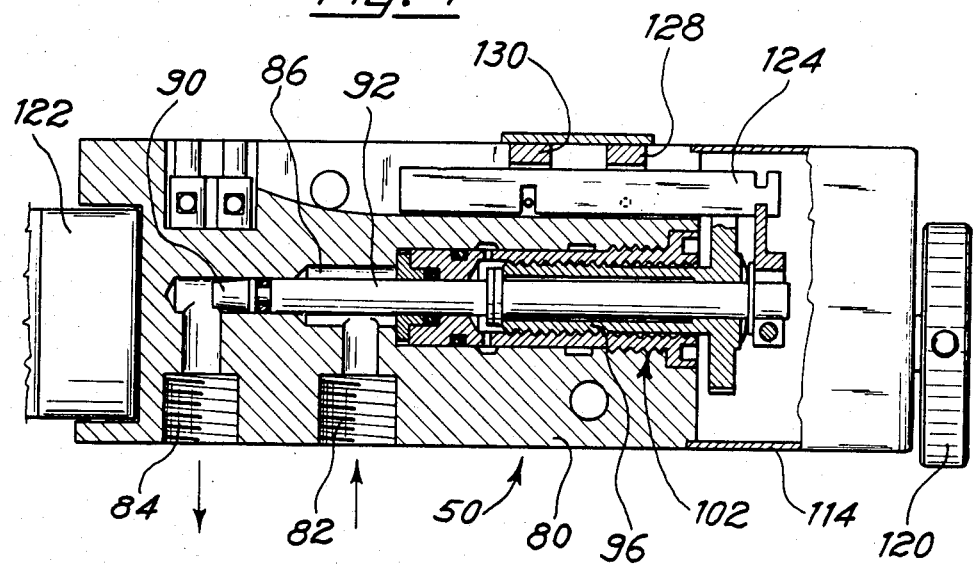

Referring to FIG. 1, apparatus for porosimetric detections comprises, as already known, a test apparatus 10, including a vessel 12 in which a solid sample 14 is placed, immersed in a liquid, usually mercury 16, the meniscus 18 of which is in a zone of reduced diameter at the mouth of vessel 12. The vessel 12 is immersed in a different liquid, for instance an oil 20 which acts on the mercury meniscus 18 as well, said oil coming from a tank 22 through two valves 24 and 26 placed on two serially connected ducts 28 and 30. The duct 28 is connected, on the side opposite to the tank 22, to the smaller cylinder 32 of a pressure multiplier 34, of known type. The large piston 36 is placed in a cylinder 38, which is fed through a duct 40 by a pump 42 sucking oil or another suitable fluid from a tank 44 through a tube 46. By pumping the low pressure fluid from pump 42 to cylinder 38, said piston 36 is moved and a pressure increase in the circuit downstream of cylinder 32 is obtained, with a pressure increase of oil 20 in the test apparatus 10. Said pressure increase compels the mercury 16 to penetrate into the pores of sample 14, with a related variation, in particular a decrease in the level of meniscus 18, which occurs and is detected as variations in pressure values, and may be correlated to trace a curve 48 (FIG. 2). From curve 48 it is possible to obtain, in a known way, sufficient data to determine some important porosimetric properties of sample 14. To obtain analytical results, it is known that pressure exercised in the high pressure circuit must reach very high values, about 2000 atmospheres, while the low pressure circuit operates taking into account that said multiplier 34 gives pressure ratios of the order of 1/100, i.e. within limits around 20 atmospheres.

The pressure reduction in the high pressure circuit, from said maximum value of about 2000 atmospheres to the ambient value, is performed by means of valve 50 acting on the low pressure circuit, in particular in a by-pass duct 52 which is connected to the tube sections 40 and 46, respectively downstream and upstream of said pump 42.

The pressure reduction involves significant importance for porosimetric analyses and particularly for the determination of the pore shape and related distribution, when the pressure reduction is performed according to a predetermined law in time. A curve of the type as shown by 54 in FIG. 2 may then be obtained, wherein said curve, together with curve 48, has a general shape of the hysteretic type. In FIG. 2, the value of 56 obviously corresponds to the amount of mercury 16 remaining in the pores of sample 14.

To perform said pressure reduction according to a predetermined variation law in time, and in particular, as preferred, at a constant pressure reduction rate, the invention proposes a pressure transducer 58 which detects at 60 the pressure in said high pressure circuit and transforms the obtained values into signals. These signals are transmitted along a line 62 to a differentiator circuit or means for differentiating which provides an output signal representing the derivative of the input signal with respect to time or a representative rate signal. This circuit, as shown by 64 in FIG. 1 is conventional and may take any of the well known forms of this conventional class of device. For instance, a classical type of differentiator circuit shown and described at Page 15 (FIG. 22) of the "Handbook of Operational Amplifier Applications", compiled by the Applications Engineering Department of Burr Brown Research Corporation, Tucson, Ariz., First Edition (second printing), Copyright 1963, may be employed. The output signal therefrom is transmitted at 66 to a window comparator 68. The window comparator 68, which may be conventional, compares said output signal with two fixed signals or reference levels, respectively, corresponding to the allowed maximum and minimum pressure reduction speeds or windows established. These two signals of the comparator 68 can be modified in a known way, either by widening or reducing the window or difference between them, or mainly by modifying their value in order to correspondingly modify the present values of pressure reduction speed. When said comparator 68 ascertains that the signal coming from line 66 exceeds or is smaller than predetermined maximum or minimum limits, respectively, either one or the other of two signals, schematically indicated by 70 and 72, is emitted as an error signal to cause the actuation of motor 74 in one direction or the other to adjust valve 50 and bring the rate of pressure reduction within the window established. The window comparator 68 may take the form of a pair of threshold detectors or comparators wherein the maximum or minimum limits are the threshold or reference values set. Such a conventional arrangement is shown, for instance, by the dual level comparator illustrated on Page 141 of the "Guidebook of Electronic Circuits", John Markus, McGraw-Hill Book Company, Copyright 1974. If this configuration were employed a separate output from each comparator would be directly utilized as outputs 70 and 72. The maximum value ($V_H$) and the minimum value ($V_L$) or limits may be selected such that the ratio of $V_H$ to $V_L$ equals a constant, for instance a value of 1.2 may be selected.

Figure 5:
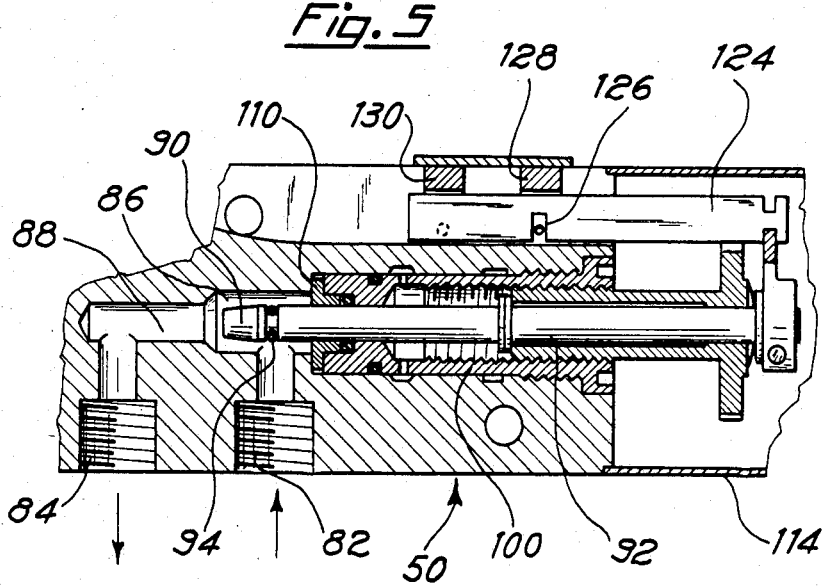
FIG. 5 is a partial cross-section of the same valve, corresponding to that of FIG. 4 but illustrating another position of the valve stem.

The valve 50 is described in greater detail in FIGS. 3 and 5 and as shown therein takes the form of a needle-type valve with a cone-shaped stem and a cylindrical seat. The stem cone angle is chosen so as to obtain a good balance between the need for quick actuation and valve precision. It is obvious that, if the cone angle is small, the response time will be slower, but greater precision will be achieved.

The illustrated valve essentially comprises a body 80 in which an input passage 82 and an exhaust passage 84 are established for the fluid employed in the low pressure circuit. The passages 82 and 84 are connected to a duct 86 where a cylindrical seat 88 is provided. A cone-shaped body 90 of the valve acts in said seat and is mounted at the end of a stem 92 capable of axially moving with respect to the cylindrical seat 88. FIGS. 3, 4, and 5 respectively show the valve stem 92 in its end positions, i.e. completely closed in FIGS. 3 and 4 and completely open in FIG. 5. However, in general, the valve is designed to operate in a position in which the cone-shaped section 90 of same only partially penetrates into the cylindrical seat 88. This leaves a small fluid blow-by area, corresponding to the desired pressure reduction speed in the low pressure circuit, and consequently, in the high pressure circuit.

The stem 92 is mounted in a rotationally free, but axially integral way inside a bushing 96, which is threaded on the outside in 98 to meet a corresponding threading of a nut screw provided in an insert 100 which in turn is connected to the body 80 of the valve by threading in 102. The insert 100 is housed in a seat 104 of the valve body with pneumatic sealing in 106 and its bottom is crossed by the stem 92. Sealing is obtained by a gasket 108 blocked by a bushing 110. The bushing 96 is integral, for instance in a single piece, with a gear wheel 112 placed in a zone outside the valve body, but protected towards the outside by a covering 114. The gear wheel 112 meshes with a pinion 116 mounted on a shaft 118 placed in parallel to the stem 92. As clearly shown in the drawing, the pinion 116 has such an axial length as to allow the gear wheel 112 to slide in the same direction along the same axis, as the bushing 96 goes up and down when the latter is turned owing to its meshing with the threading 98. The shaft 118 can be rotated manually, by means of a control handle 120, acting in emergency, but it is usually controlled in its rotations by a geared motor 122 which is conventional, corresponding to the motor means 74 of FIG. 1. Obviously, said geared motor can rotate in both directions to cause rotations in both directions of the pinion 116 and of the wheel 112, as well as of the bushing 96, with corresponding upward and downward axial movements of same together with the stem 92 which opens or closes the valve seat 88. The axial movements of stem 92 control the passage area of the low pressure fluid between the inlet 82 and outlet 84. The movements of stem 92 are controlled, as previously seen, by a detection performed on the high pressure circuit so as to maintain the pressure reduction speed within given limits. In this way it is possible to obtain a pressure reduction speed in the high pressure circuit which ranges from values of 1 bar/sec to values of 20 bar/sec, with a single type of valve design, that is with the same exhaust valve and therefore with the same analytical equipment.

With reference to FIGS. 4 and 5, the stem 92 is provided outside the valve body 80, with a plate 124 which moves parallely to the stem itself out of the valve body 80 and bears means for delimiting the run of stem 92, between the valve's completely closed position and completely open position. Said means can be constituted by an opening 126, which cooperates with two detectors 128 and 130, for instance photodiodes, to determine the positions of maximum closure (FIG. 4) and maximum opening (FIG. 5). Said valve has proved to be particularly precise and of particularly quick actuation, so that it is possible to consider that a pressure reduction in the high pressure circuit is performed, by said control, at a constant speed, in a way that the curve 54 of FIG. 2 can be traced and related conclusions can be drawn from it about further porosimetric properties of sample 14, nondetectable from curve 48 alone.

As it will be clear to those skilled in the art, the invention can be carried-out in different ways, all coming within the scope of the present invention.

What is claimed is:

1. Apparatus for porosimetric determinations comprising:
   test chamber means for holding a sample and a liquid, said liquid for penetrating pores in said sample;
   means for increasingly applying pressure to said liquid in said test chamber means to force said liquid into said pores in said sample, said means for increasingly applying pressure acting to increase pressure applied to said liquid until a selected pressure is reached; and
   means for decreasing pressure applied to said liquid to permit said liquid to withdraw from said pores in said sample, said means for decreasing pressure acting to reduce pressure on said liquid from said selected pressure to a predetermined minimum pressure at a substantially constant rate in time throughout a given pressure range.

2. The apparatus according to claim 1 additionally comprising means for detecting variations in volume of said liquid due to liquid entering and exiting pores in said sample with changes in pressure.

3. The apparatus according to claim 1 wherein said means for decreasing pressure applied to said liquid includes:
   means for measuring pressure applied to said liquid and providing an output signal representative of said pressure measured;
   means for differentiating said output signal to obtain a representative rate signal;
   means for comparing said representative rate signal to predetermined maximum and minimum values corresponding to selected maximum and minimum pressure reduction rates; and
   means responsive to said means for comparing for varying pressure applied to said liquid to bring said representative rate signal within said selected maximum and minimum pressure reduction rates.

4. The apparatus according to claim 1 wherein said means responsive to said means for comparing for varying pressure applied to said liquid includes motor driven valve means.

5. The apparatus according to claim 4 wherein said motor driven valve means includes motor means and needle valve means, said motor means including a driving shaft rotatable in both directions to selectively open and close said needle valve means and said needle valve means including a needle valve stem having a cone-shaped end in said needle valve means, said needle valve means having a cylinderical seat for said needle valve stem and said driving shaft rotation deplacing said needle valve stem in said cylinderical seat to control fluid passage between said cone-shaped end and said cylinderical seat.

6. The apparatus according to claim 5 wherein said shaft is connected to said needle valve stem through a screw and nut coupling to transform the rotary movements of said driving shaft into axial movements of said needle valve stem.

7. A method for performing porosimetric analysis comprising the steps of:
   immersing a sample whose porosity characteristics are to be measured in a liquid within a test chamber;
   increasingly applying pressure to said liquid in said test chamber to force said liquid into said pores in said sample, said step of increasingly applying pressure to said liquid continuing until a selected maximum pressure is reached;
   determining the volume of liquid in said test chamber as pressure is increasingly applied to said liquid;
   decreasing pressure applied to said liquid to permit said liquid to withdraw from said pores in said sample, said step of decreasing pressure being conducted in a manner to reduce the pressure applied to said liquid at a substantially constant rate from said selected maximum pressure to a predetermined minimum pressure; and
   ascertaining the volume of liquid in said test chamber as pressure on said liquid is decreased at a constant rate from said selected maximum pressure to said predetermined minimum pressure.

8. Apparatus for porosimetric determinations comprising:
   test chamber means for holding a sample and a liquid, said liquid for penetrating pores in said sample;
   a high pressure circuit for applying pressure to said liquid in said test chamber means, said high pressure circuit containing a pressuring fluid and subjecting said liquid to pressures exhibited by said pressuring fluid;
   pressure multiplier means for multiplying pressure exhibited by a low pressure fluid and imposing said multiplied pressure on said pressuring fluid within said high pressure circuit;
   a low pressure circuit for applying said low pressure fluid to said pressure multiplier means to increase the amount of pressure on said pressuring fluid to a predetermined maximum value and removing said low pressure fluid from said pressure multiplier means to decrease the amount of pressure on said pressuring fluid to a selected minimum value; and
   control means for said low pressure circuit, said control means active during a removal of low pressure fluid from said pressure multiplier means to cause the amount of pressure on said pressuring fluid to decrease at a substantially constant rate from said maximum value to said selected minimum value.

9. The apparatus according to claim 8 wherein said low pressure circuit includes pump means for said low pressure fluid and said control means includes means for measuring pressure imposed on said pressuring fluid, said means for measuring pressure providing an output signal representative of said pressure measured, means for differentiating said output signal to obtain a representative rate signal, means for comparing said representative rate signal to a selected pressure reduction rate value to obtain an error signal, and means responsive to said error signal for adjusting flow of low pressure fluid between said pump means and said pressure multiplier means.

10. The apparatus according to claim 9 wherein said means for adjusting flow includes motor driven valve means.

11. The apparatus according to claim 9 wherein said means for comparing said representative rate signal to a selected pressure reduction rate value acts to compare said representative rate signal to predetermined maximum and minimum values corresponding to selected maximum and minimum pressure reduction rates, and said means responsive to said error signal for adjusting acts to vary pressure applied to said low pressure fluid to bring said representative rate signal within said selected maximum and minimum pressure reduction rates.

12. The apparatus according to claim 10 wherein said motor driven valve means is disposed in a by-pass arrangement for said pump means.

13. The apparatus according to claim 10 wherein said motor driven valve means includes motor means and needle valve means, said motor means including a driving shaft rotatable in both directions to selectively open and close said needle valve means and said needle valve means including a needle valve stem having a cone-shaped end in said needle valve means, said needle valve means having a cylinderical seat for said needle valve stem and said driving shaft rotation deplacing said needle valve stem in said cylinderical seat to control fluid passage between said cone-shaped end and said cylinderical seat.

* * * * *

UNITED STATES PATENT AND TRADEMARK OFFICE
CERTIFICATE OF CORRECTION

PATENT NO. : 4,644,779

DATED : February 24, 1987

INVENTOR(S) : Sisti, et al

It is certified that error appears in the above-identified patent and that said Letters Patent is hereby corrected as shown below:

Column 5, line 50, "claim 1" should read --claim 3--.

Signed and Sealed this

Eighteenth Day of August, 1987

*Attest:*

DONALD J. QUIGG

*Attesting Officer*   *Commissioner of Patents and Trademarks*